United States Patent [19]
Matsumaru

[11] Patent Number: 5,174,277
[45] Date of Patent: Dec. 29, 1992

[54] ENDOSCOPE
[75] Inventor: Takafumi Matsumaru, Tokyo, Japan
[73] Assignee: Kabushiki Kaisha Toshiba, Kawasaki, Japan
[21] Appl. No.: 644,604
[22] Filed: Jan. 23, 1991
[30] Foreign Application Priority Data Jan. 24, 1990 [JP] Japan .................................. 2-12443

[51] Int. Cl.⁵ .............................................. A61B 1/00
[52] U.S. Cl. ...................................................... 128/4
[58] Field of Search .................... 128/4, 6, 7; 73/151; 138/120

[56] References Cited
U.S. PATENT DOCUMENTS

3,190,286  6/1965  Stokes .................................. 128/6
3,266,059  8/1966  Stelle ................................... 128/4
3,669,098  6/1972  Takahasi .............................. 128/6
4,347,837  9/1982  Hosono ............................... 128/6
4,655,257  4/1987  Iwashita ........................... 128/4 X Primary Examiner—Gene Mancene
Assistant Examiner—Thomas Price
Attorney, Agent, or Firm—Foley & Lardner

[57] ABSTRACT

An endoscope has a flexible section. The flexible section comprises a plurality of articular rings connected to one another, and are movable relative to one another. The axial length of at least one of the articular rings is different from the axial length of the others. Wire guides are disposed in the articular rings, and wires are passed through the wire guides. The wires are operated to bend the flexible section.

28 Claims, 10 Drawing Sheets

ENDOSCOPE

BACKGROUND OF THE INVENTION

1. Field of the Invention

The present invention relates to an endoscope having a flexible section, and particularly to endoscopes having flexible sections of various forms and operation forces.

2. Description of the Prior Art

Figure 1:
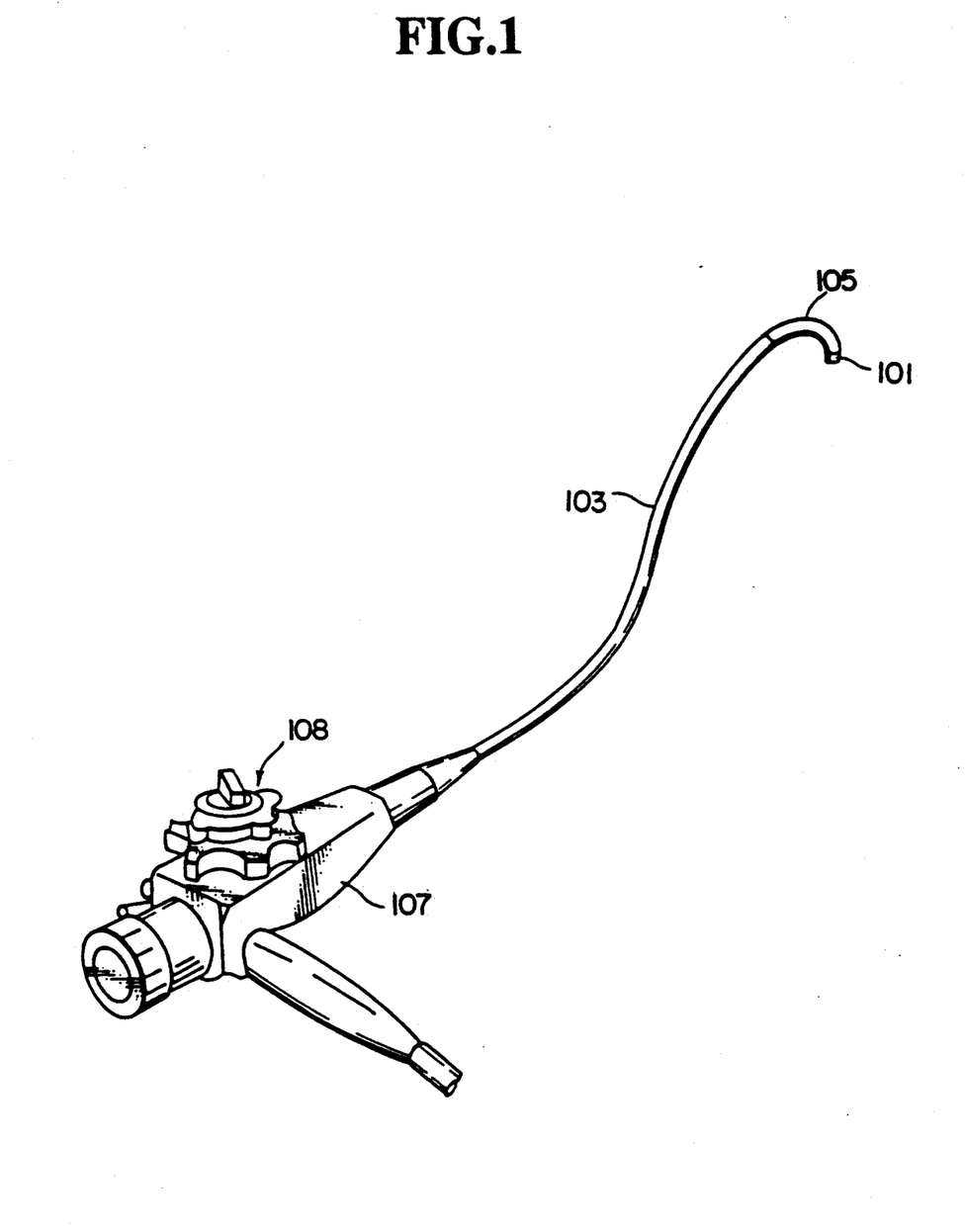
FIG. 1 is a perspective view showing a conventional endoscope.

FIG. 1 shows a conventional endoscope. The endoscope comprises a front end 101 having an observation window, an illumination window, a forceps mouth, etc., for observing and treating celomic sites, a flexible tube 103, a flexible section 105 disposed between the front end 101 and the flexible tube 103, and a controller 107 disposed at the other end of the flexible tube 103 to curve the flexible section 105.

The flexible section 105 comprises a plurality of articular rings that are connected to one another through joints. The articular rings can pivot around the joints, and have wire guides through which wires are passed. In each of the articular rings, the wire guides are equally and oppositely distanced from an axis of the articular ring in a diametral direction.

When one of the wires is pulled and the other released through an operation mechanism 108 of the controller 107, the flexible section 105 curves. At this time, the front end 101 curves along an arc of large radius whose center is positioned close to the flexible tube 103, so that the front end 101 may hit a celomic site to stop curving or to injure an internal wall of the celomic site.

Figure 2:
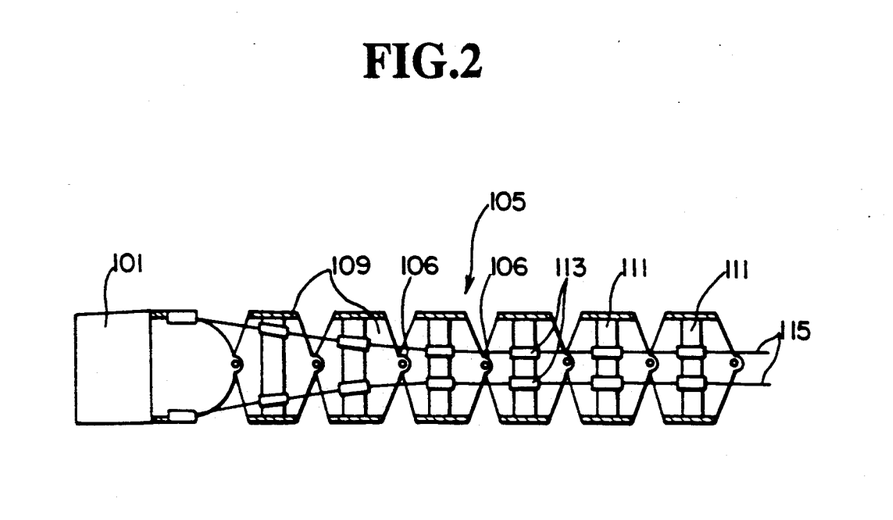
FIG. 2 is a longitudinal section showing a flexible section of an endoscope according to a prior art.

To deal with this problem, Japanese Utility Model Publication No. 60-41206 proposes a flexible section 105 of FIG. 2. The flexible section 105 comprises articular rings 109 each having a fitting plate 111 extending along a diameter of the articular ring. The fitting plate 111 has a pair of wire guides 113. Diametral distances between the wire guides 113 of the respective articular rings 109 become larger from a rear end of the flexible section 105 toward a front end 101.

Figure 3:
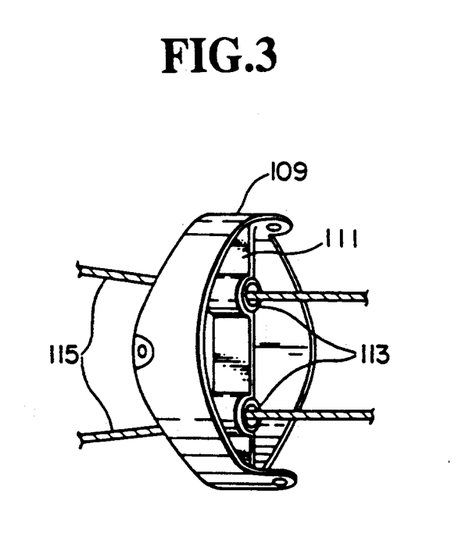
FIGS. 3 and 4 are enlarged perspective views showing essential parts of the flexible section of FIG. 2.
Figure 4:
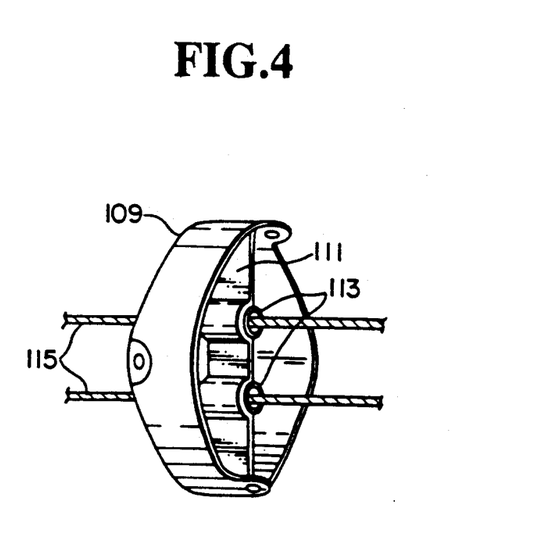

FIG. 3 shows the articular ring 109 positioned close to the front end 101, and FIG. 4 the articular ring 109 positioned away from the front end 101.

When wires 115 passing through the wire guides 113 move, the articular ring 109 in the vicinity of the front end 101 receives a large angular moment, so that the flexible section 105 may curve from the front end portion at a small radius of curvature.

Figure 5:
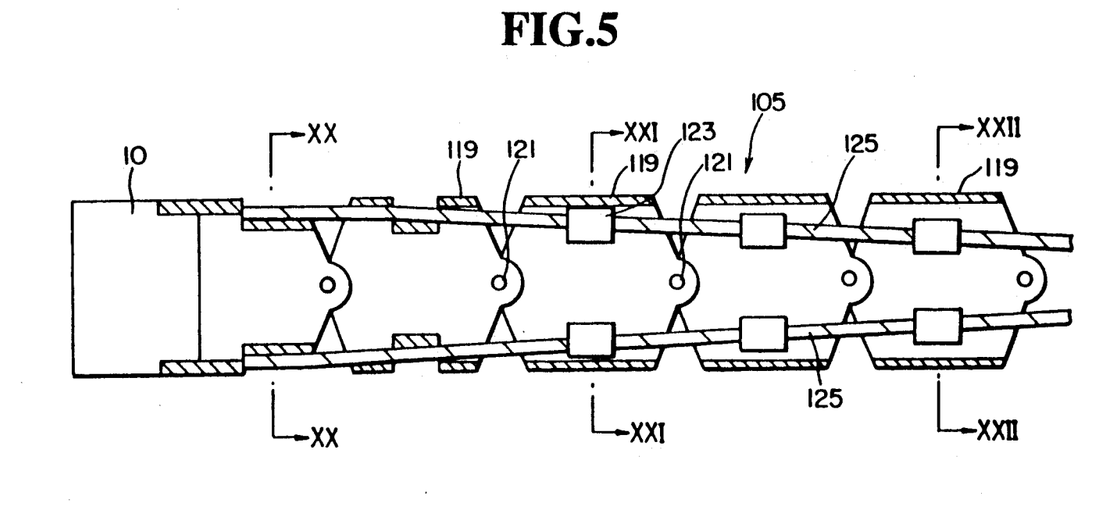
FIG. 5 is a longitudinal section showing a flexible section of an endoscope according to a prior art.

FIG. 5 is a sectional view showing a flexible section 105 disclosed in Japanese Laid-Open Patent Publication No. 62-281918. This flexible section 105 has articular rings 119 each having wire guides 123. The articular rings 119 are connected to one another through joints 121.

Figure 6:
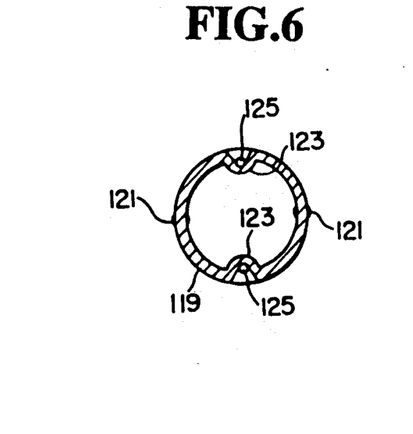
FIG. 6 is a cross-sectional view taken along a line XX of FIG. 5.
Figure 7:
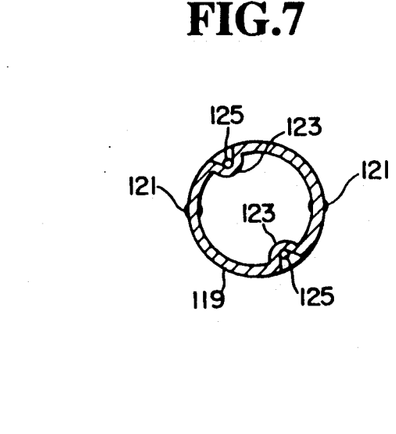
FIG. 7 is a cross-sectional view taken along a line XXI of FIG. 5.
Figure 8:
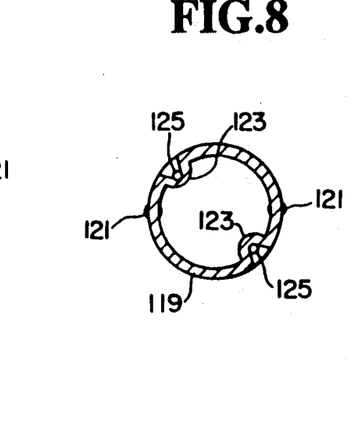
FIG. 8 is a cross-sectional view taken along a line XXII of FIG. 5.

FIG. 6 is a cross-sectional view showing the articular ring 119 positioned close to a front end 10 of FIG. 5. In this articular ring 119, the wire guides 123 are farthest from the joints 121 of this articular ring compared with those in the other articular rings 119. The wire guides 123 of the respective articular rings 119 gradually approach their corresponding joints 121 from the front end 10 toward a rear end of the flexible section 105 as showing in FIGS. 5 to 8.

When wires 125 passing through the wire guides 123 move, the articular ring 119 in the vicinity of the front end 10 receives a larger angular moment than the articular ring 119 in the vicinity of the rear end, so that the flexible section 105 may curve from the front end side at a small radius of curvature.

In these conventional flexible sections 105, a distance between any adjacent two joints 106 or 121 is identical, so that the conventional flexible sections 105 may provide only a few variations of curved shapes.

Namely, the conventional flexible sections cannot provide a sufficiently small radius of curvature at front ends thereof, and cannot gradually curve from rear ends thereof.

According to the Japanese Utility Model Publication No. 60-41206, the flexible section 105 has the fitting plates 111 each extending along the whole diameter of the articular ring 109. The fitting plates 111 narrow the insides of the articular rings 109 so that the wires 115, observation and illumination fibers, and various tubes may not easily be positioned inside the articular rings 109, thereby reducing a filling ratio of the articular rings 109 and complicating the articular rings 109.

According to the Japanese Laid-Open Patent Publication No. 62-281918, the wire guides 123 gradually approach the joints 121 in the articular rings 119 from the front end side toward the rear end side of the flexible section 105. Namely, the wire guides 123 and wires 125 are not arranged straight but twisted in a longitudinal direction. The wires 125, therefore, must be strongly pulled to curve the articular rings 119 because this arrangement consumes an unnecessary force in bending. Compared with a straight arrangement of wires and wire guides, the twisted arrangement is not efficient in bending the flexible section 105.

Namely, the spirally arranged wire guides 123 inevitably increase a force to be applied to the wires 125 in a bending operation as well as frictional force between the wires 125 and the wire guides 123, thereby shortening their service lives.

Due to the twisted arrangement of the wire guides 125, not only the wires 125 but also the observation and illumination fibers and various tubes which are observation and operation means and disposed inside the articular rings 119 change their diametral positions along a longitudinal axis by sliding spirally during the curving operation. This increases an apparent flexural rigidity of the flexible section 105, thereby increasing a bending force and a wire operating force to relatively easily break the fibers and tubes.

In addition, arranging the wire guides 123 successively at spiral positions in the articular rings 119 increases the number of processes, time and labor in manufacturing the endoscope.

In this way, the flexible sections of conventional endoscopes comprise articular rings of identical size, and wire guides disposed at regular positions so that they may provide only a few variations of final curved shapes. In addition, the conventional flexible sections require a large force for operating the wires in curving the flexible sections, thereby deteriorating operability of the endoscopes and shortening service lives of the wires and wire guides due to abrasion.

SUMMARY OF THE INVENTION

An object of the present invention is to provide endoscopes with flexible sections of various forms that may be selected depending on a purpose of use.

Another object of the present invention is to provide an endoscope having a flexible section that curves with a small wire operating force, the flexible section comprising articular rings in which wires, observation and illumination fibers, and various tubes slide straightly.

In order to accomplish the objects, the present invention provides an endoscope having a flexible section that comprises a plurality of articular rings. The articular rings are connected to one another such that they can pivot relative to one another. The articular rings have wire guides for passing wires. The wires are operated to curve the flexible section. The axial length of at least one of the articular rings is different from that of the others.

According to another aspect of the present invention, a flexible section of an endoscope comprises a plurality of articular rings that are connected to one another such that they can pivot relative to one another. The articular rings have wire guides for passing wires. The wires are operated to curve the flexible section. The positions of the wire guides of at least one of the articular rings are axially different from the positions of the wire guides of the other articular rings in the axially direction of the rings.

With different axial lengths of the articular rings, or with axially shifted positions of the wire guides, different forces act on the respective articular rings. Namely, the present invention changes axial lengths or positions of the articular rings, thereby providing flexible sections of different curves and different wire operating forces.

These and other objects, features and advantages of the present invention will be more apparent from the following detailed description of preferred embodiments in conjunction with the accompanying drawings.

DETAILED DESCRIPTION OF THE EMBODIMENTS

Figure 9:
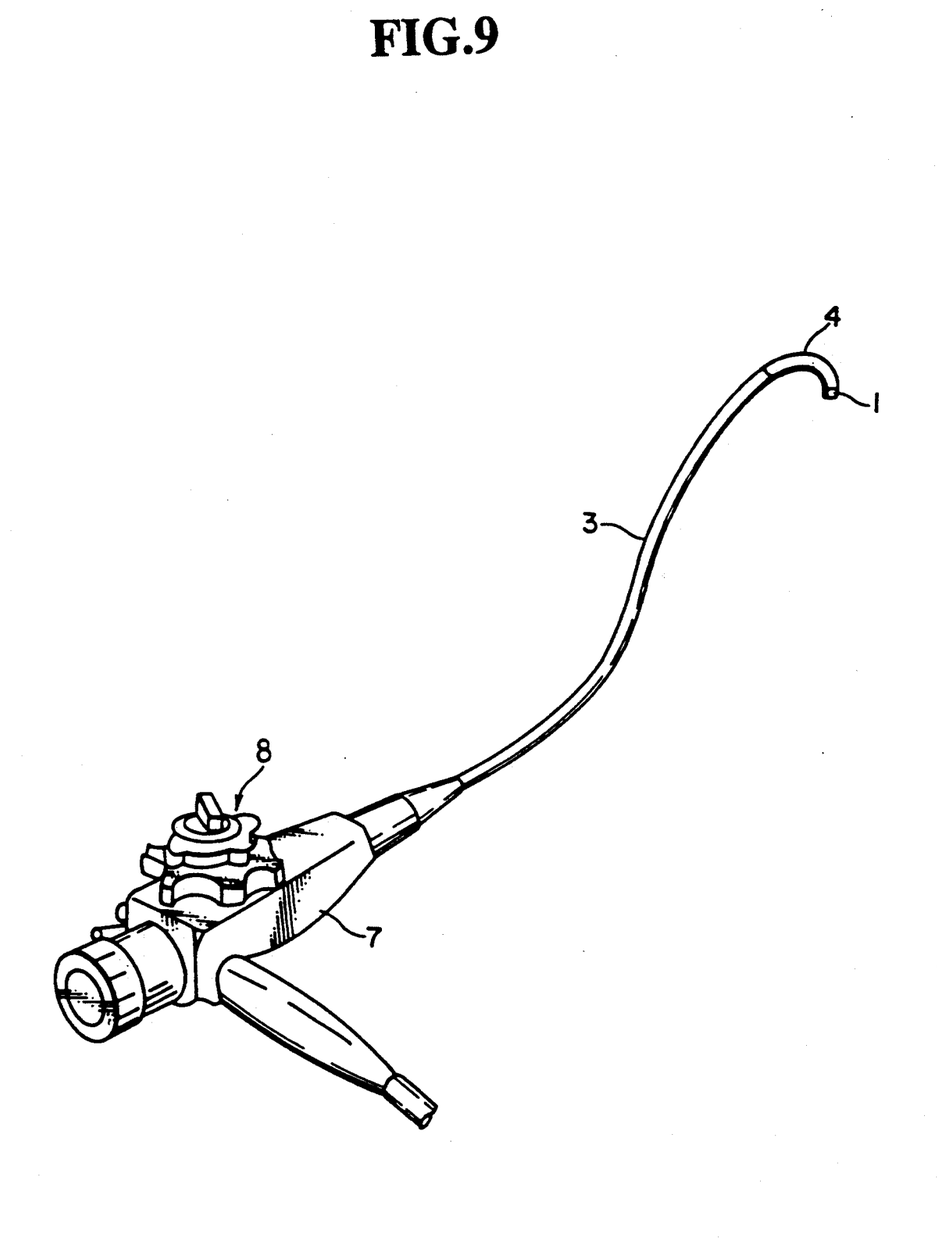
FIG. 9 is a perspective view showing an endoscope employing a flexible section according to the present invention.

FIG. 9 is a perspective view showing an endoscope having a flexible section 4 according to the present invention. The endoscope comprises a front end 1 having an observation window, an illumination window, a forceps mouth, etc., a flexible tube 3, and the flexible section 4 disposed between the front end 1 and the flexible tube 3. A controller 7 is fitted to the other end of the flexible tube 3. The controller 7 has an operation mechanism 8 with which wires 9 (FIG. 10, for example) are pulled or released to curve the flexible section 7.

Figure 10:
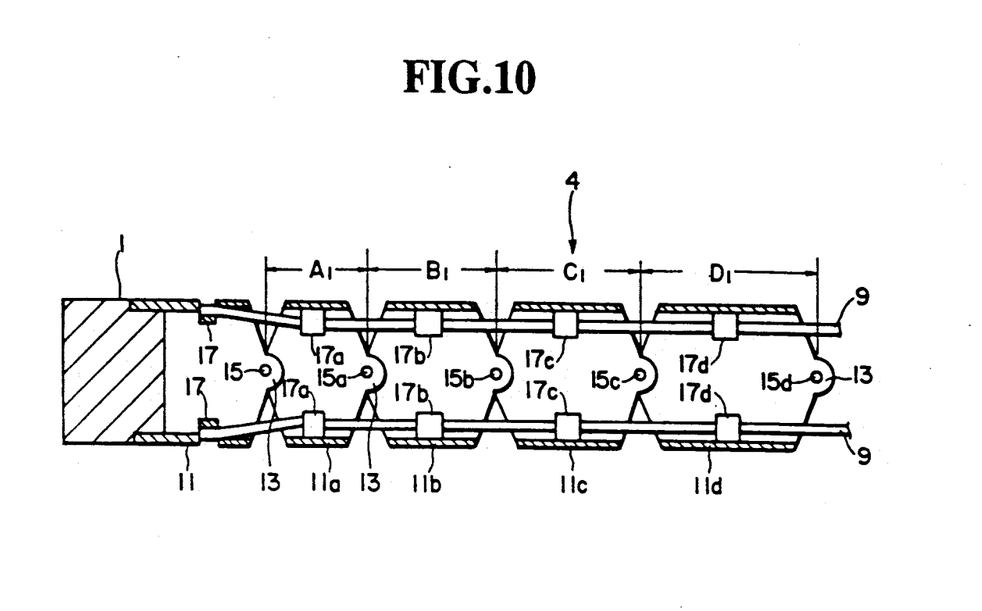
FIG. 10 is a longitudinal section showing a flexible section of an endoscope according to a first embodiment of the present invention.

FIG. 10 shows an endoscope flexible section 4 according to the first embodiment of the present invention. The flexible section 4 comprises a plurality of articular rings 11 to 11d having protruding end faces that form connecting portions 13. The connecting portions 13 are connected to one another with joints 15 to 15d so that the articular rings may pivot relative to one another.

The first articular ring 11 is fixed to the front end 1, and the last articular ring 11d is connected to the flexible tube 3.

Each end face of each of the articular rings 11 to 11d has a tapered shape or an arc shape such that the height of a peripheral wall of the end face decreases from the center toward the diametral outside to form a gap between adjacent articular rings, thereby enabling the articular rings to move relative to each other within a limited range.

Hollow cylindrical wire guides 17 to 17d are disposed on the inner walls of the articular rings 11 to 11d, respectively. In each of the articular rings, the wire guides are separated from each other by about 180 degrees.

Through this specification, only those elements that are necessary for movements in the plane of each drawing are shown.

A distance A1 from the first joint 15 to the second joint 15a of the articular ring 11a is shortest among inter-joint distances A1 to D1 of the articular rings 11a to 11d. The closer one articular ring is positioned to a rear end of the flexible section 4, the shorter the inter-joint distance of the one articular ring becomes.

Namely, the inter-joint distances of FIG. 10 have a relation of "A1<B1<C1<D1."

Wires 9 pass through the upper and lower wire guides 17 to 17d. One ends of the wires 9 are connected to the operation mechanism 8 of the controller 7, and the other ends thereof are fixed by soldering, etc., to the wire guides 17 disposed on the articular ring 11 that is integral with the front end 1.

An operation of the first embodiment will be explained.

The endoscope is inserted into the celomic of a patient to observe or treat a celomic site. The operation mechanism 8 pulls or releases the wires 9, thereby curving the flexible section 4 to orient the front end 1 toward the celomic site.

Among the joints 15 to 15d, the joint 15d is subjected to a largest angular moment because the distance D1 from the joint 15d to the next joint 15c is the longest among the inter-joint distances A1 to D1. The flexible section 4 firstly curves, therefore, around the joint 15d.

Figure 11:
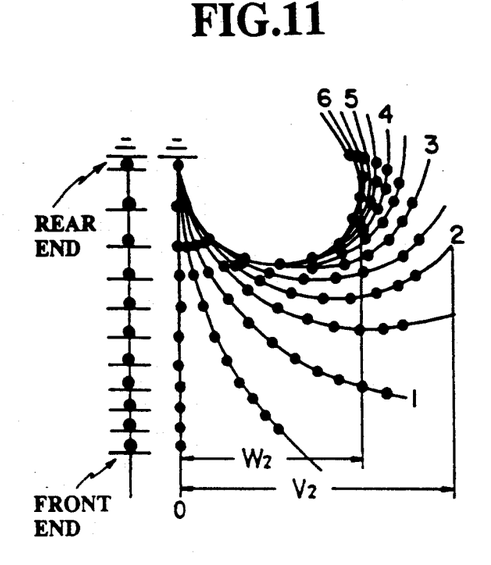
FIG. 11 is a graph of test results showing curved shapes of the embodiment of FIG. 10.
Figure 12:
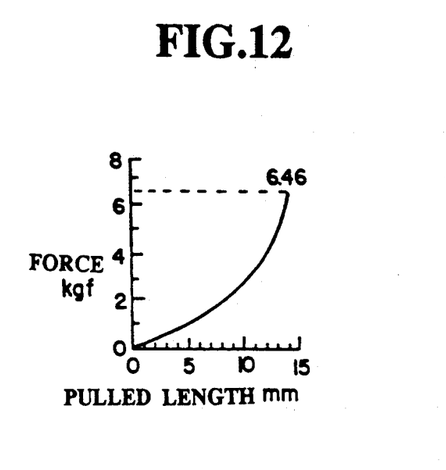
FIG. 12 is a graph of test results showing a relationship between pulled lengths and operating forces of a wire of the embodiment of FIG. 10.

FIG. 11 is a graph of test results showing curved shapes of the flexible section 4 of FIG. 10 in response to pulled lengths (shifts) of the wire 9 changing from zero to 1, 2, and so on. FIG. 12 is a graph of test results showing a relationship between pulled lengths of the wire 9 and forces applied to the wire 9.

Figure 13:
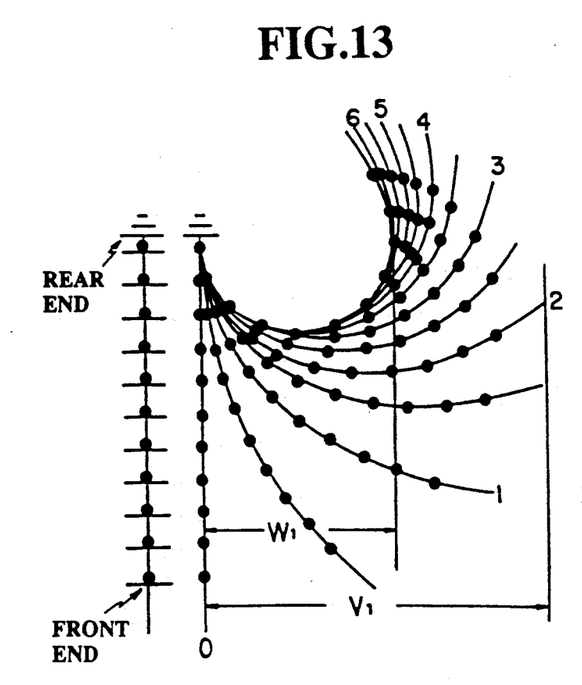
FIG. 13 is a graph of test results showing curved shapes of a comparison example.
Figure 14:
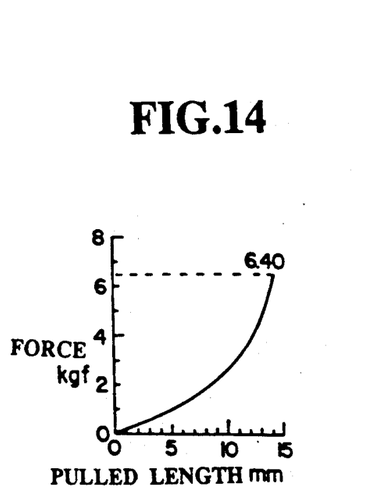
FIG. 14 is a graph of test results showing a relationship between pulled lengths and operating forces of a wire of the comparison example.

FIG. 13 is a graph of test results showing curved shapes of a flexible section of a comparison example, and FIG. 14 is a graph of test results showing a relationship between pulled lengths and applied forces of a wire in the comparison example. This comparison example (not shown) has the same total length and the same number of joints as those of the flexible section 4 of FIG. 10. The comparison example has, however, an identical inter-joint distance in articular rings thereof.

As is apparent in FIG. 11, the flexible section 4 of the present invention curves sequentially from the last joint 15d toward the first joint 15a up to each maximum curve angle determined by the end face shape of each articular ring, as the pulled length of the wire 9 increases.

Compared with the comparison example of FIG. 13, the closer one articular ring is positioned to the front end 1 in the present invention of FIG. 11, the smaller a radius of curvature for the one articular ring becomes. In a final curved shape of FIG. 11 of the present invention, a smallest radius of curvature appears on the front end side.

As explained before, the two examples of FIGS. 11 and 13 have the same total length, the same number of joints, and the same maximum curving angle for each articular rings. In the embodiment of the present invention of FIG. 11, the last articular ring 11d having the longest inter-joint distance D1 firstly curves to its maximum extent, then the next articular ring 11c, and so on. This way of curving provides a small radius of curvature at the front end 1 of the flexible section 4. A width V2 from an initial straight posture to a maximum reach of the front end 1 of the present invention of FIG. 11 is shorter than a corresponding width V1 of the comparison example of FIG. 13. Also, the final curved shape of the flexible section 4 of the present invention has a small radius of curvature at the front end and a large radius of curvature at the rear end. A width W2 from the initial straight shape to the outermost part of the flexible section 4 in the final curved shape is shorter than a corresponding width W1 of the comparison example of FIG. 13.

Figure 15:
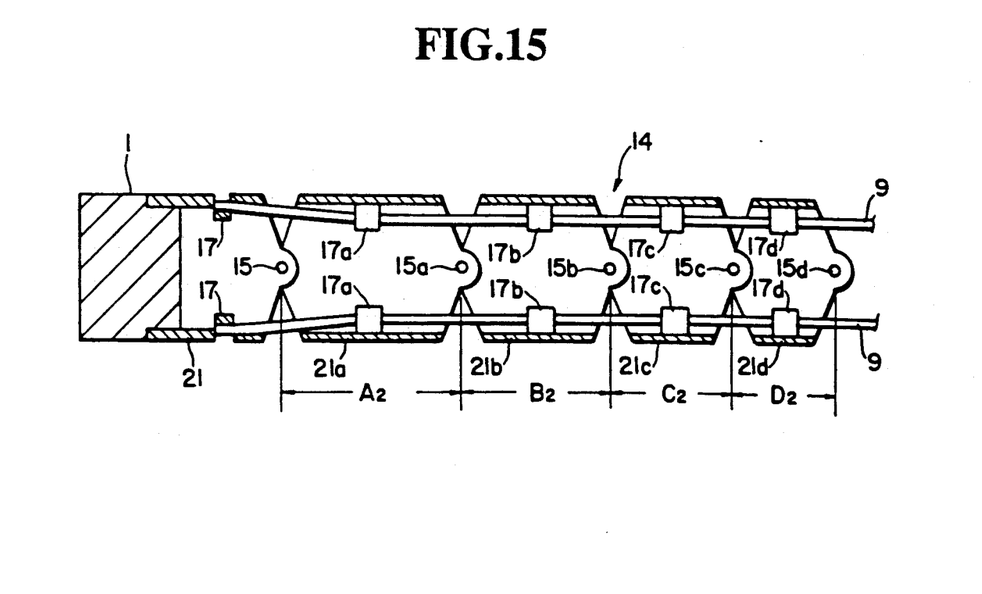
FIG. 15 is a longitudinal section showing a flexible section of an endoscope according to a second embodiment of the present invention.

FIG. 15 is a longitudinal section showing a flexible section 14 according to the second embodiment of the present invention. In FIG. 15, the same parts as those of the first embodiment of FIG. 10 are represented with like numerals, and their explanations are omitted.

According to the second embodiment, the flexible section 14 comprises articular rings 21 to 21d. An inter-joint distance A2 between a front joint 15 of the first articular ring 21a and a rear joint 15a thereof is the longest among inter-joint distances A2 to D2 of the articular rings 21a to 21d. The closer one articular ring is positioned to a rear end of the flexible section 14, the shorter the inter-joint distance of the one articular ring becomes.

Namely, the inter-joint distances of FIG. 15 have a relation of "A2>B2>C2>D2."

Figure 16:
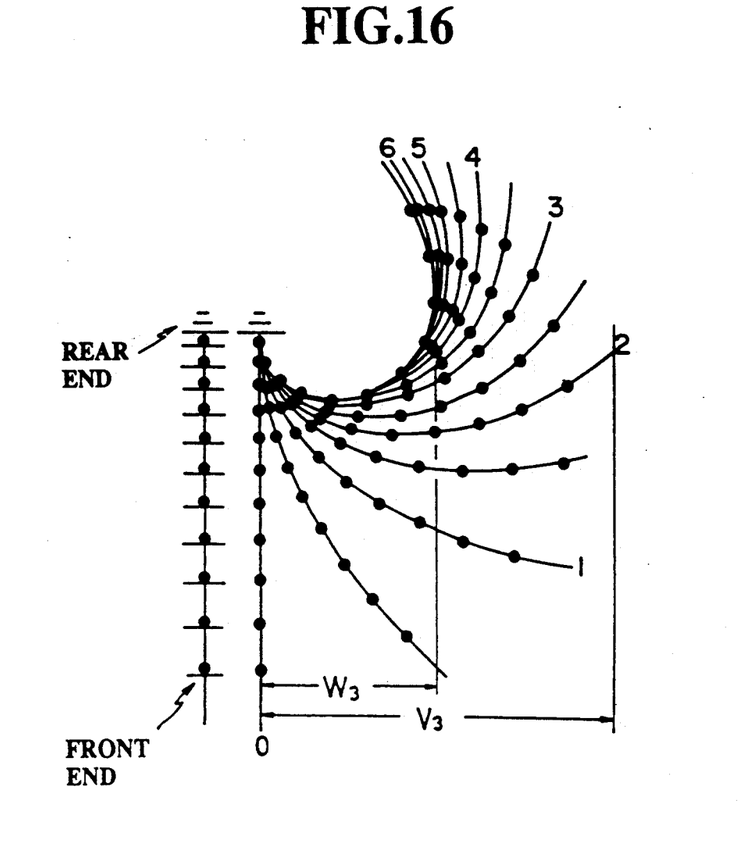
FIG. 16 is a graph of test results showing curved shapes of the second embodiment of FIG. 15.

When one of wires 9 passing through wire guides 17 to 17d is pulled, the flexible section 14 starts to curve firstly around the last joint 15d, then around the next joint 15c, and so on, each time up to a maximum curve angle determined by an end face shape of the corresponding articular ring, thereby providing curved configurations of FIG. 16.

Compared with the comparison example of FIG. 13, the closer one articular ring of the second embodiment of FIG. 15 is positioned to a front end portion, the larger a radius of curvature of the one articular ring becomes, because of a longer inter-joint distance. A width V3 of the maximum reach of the second embodiment is, therefore, longer than the corresponding width V2 of the comparison example of FIG. 13. The final curved shape of the second embodiment has a small radius of curvature at the rear end thereof where the inter-joint distance is short, so that a width W3 of the curved shape of the second embodiment is shorter than the corresponding width W1 of the comparison example of FIG. 13.

Figure 17:
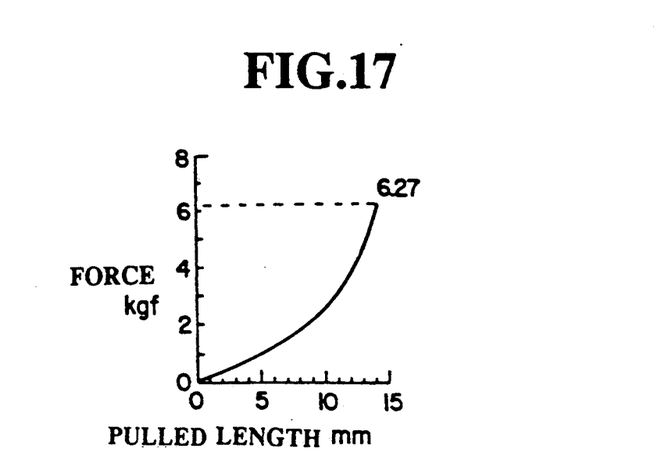
FIG. 17 is a graph of test results showing a relationship between pulled lengths and operating forces of a wire of the second embodiment.

A final wire operating force of the flexible section 14 of the second embodiment is 6.27 Kg as shown in FIG. 17. This value is smaller than 6.46 Kg of the first embodiment of FIG. 12, and 6.40 Kg of the comparison example of FIG. 14. This is because a distance between joints becomes longer toward the front end side of the flexible section 14 to curve with a small moment in the second embodiment.

As explained in the first and second embodiments, distances between joints of respective articular rings that form a flexible section may properly be changed to provide specific curved shapes and wire operating forces.

Figure 18:
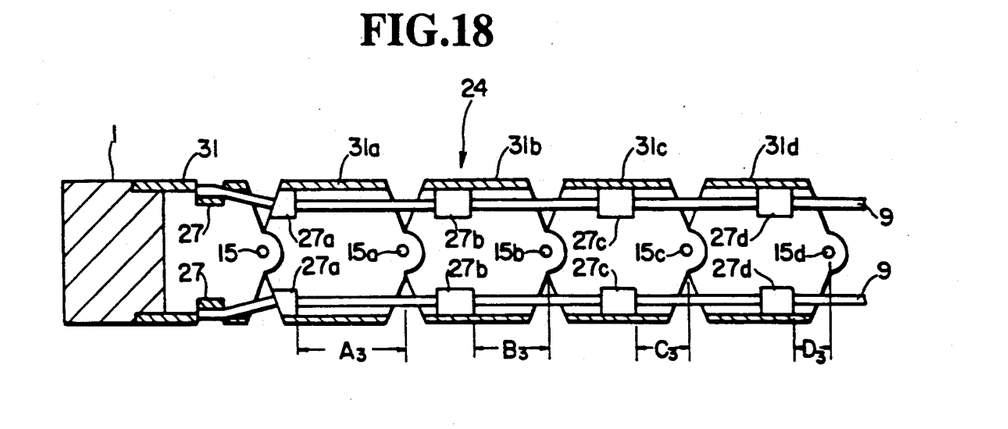
FIG. 18 is a longitudinal section showing a flexible section of an endoscope according to a third embodiment of the present invention.

FIG. 18 is a longitudinal section showing a flexible section 24 according to the third embodiment of the present invention. In FIG. 18, the same parts as those of the first embodiment of FIG. 10 are represented with like numerals, and their explanations are omitted.

According to the third embodiment, the flexible section 24 comprises articular rings 31 to 31d. Inter-joint distances of the articular rings 31 to 31d are identical. The articular rings 31 to 31d have wire guides 27 to 27d, respectively. The wire guides 27a of the articular ring 31a are distanced farthest from a corresponding rear joint 15a, compared with the other wire guides. The closer one articular ring is positioned to a rear end of the flexible section 24, the closer the wire guides of the one articular ring approach a corresponding rear joint. In other words, the positions of the wire guides of at least one of the articular rings are axially different from the positions of the wire guides of the other articular rings in the axially direction of the rings.

Namely, distances A3 to D3 between the wire guides and the rear joints have a relation of "A3>B3>C3>D3."

Similar to the first and second embodiments, when one of wires 9 passing through the wire guides 27 to 27d is pulled, the flexible section 24 of the third embodiment starts to curve from the last joint 15d sequentially to the first joint 15a, each time up to a maximum curve angle determined by the end face shape of each articular ring. Since the distance from the wire guides to the corresponding rear joint becomes longer as the articular ring comes closer to a front end 1 of the flexible section 24, a larger bending moment is applied to the articular ring which is closer to the front end. Namely, the closer one articular ring is positioned to the front end 1, the easier the one articular ring bends. This reduces a wire operating force in the final curved state of the flexible section 24.

Figure 19:
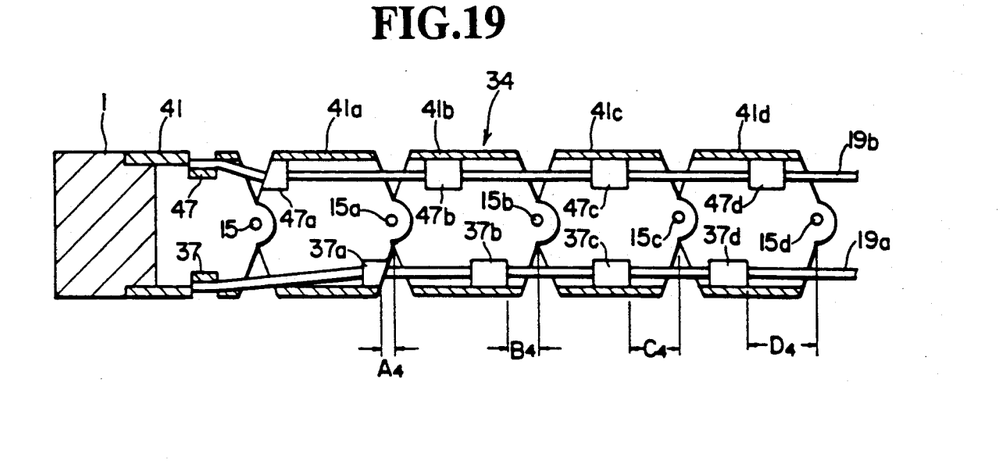
FIG. 19 is a longitudinal section showing a flexible section of an endoscope according to a fourth embodiment of the present invention.

FIG. 19 is a longitudinal section showing a flexible section 34 according to the fourth embodiment of the present invention. In this figure, the same parts as those of the third embodiment of FIG. 18 are represented with like numerals, and their explanations are omitted.

According to the fourth embodiment, the flexible section 34 comprises articular rings 41 to 41d having first wire guides 37 to 37d and second wire guides 47 to 47d. The first wire guides 37 to 37d pass a first wire 19a, and the second wire guides 47 to 47d pass a second wire 19b. The closer one articular ring is positioned to a rear end of the flexible section 34, the farther the first wire guide of the one articular ring separates from a rear joint of the one articular ring. In other words, the positions of the wire guides of at least one of the articular rings are axially different from the positions of the wire guides of the other articular rings in the axially direction of the rings.

Namely, distances A4 to D4 between the first wire guides and the respective rear joints have a relation of "A4<B4<C4<D4."

The second wire guides 47 to 47d are arranged in the same manner as in the third embodiment of FIG. 18.

When the first wire 19a is pulled, the articular rings 41 to 41d successively pivot firstly around the joint 15d up to the joint 15a, each time up to a maximum curved shape defined by an end face shape of each articular ring as in the previous embodiments. Since the first wire guides 37 to 37d are arranged such that the closer one articular ring to the rear end of the flexible section 34, the farther the first wire guide of the one articular ring from the rear joint of the one articular ring, a first force applied to the wire 19a effectively curves the flexible section 34. Namely, the flexible section 34 may curve largely with an initial small operating force. As a result, a total wire operating force of the flexible section 34 in a final maximum curved shape is also small.

In pulling the first wire 19a, the wire operating force sharply increases with respect to a wire pulled length in the final stage of curving. In pulling the second wire 19b, the wire operating force smoothly increases relative to a wire pulled length, thereby improving operability.

Figure 20:
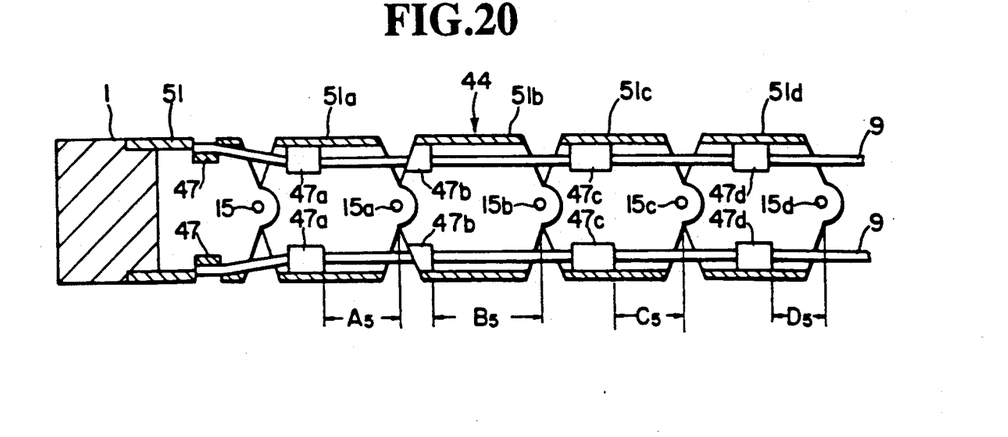
FIG. 20 is a longitudinal section showing a flexible section of an endoscope according to fifth embodiment of the present invention.

FIG. 20 is a longitudinal section showing a flexible section 44 according to the fifth embodiment of the present invention. In this figure, the same parts as those of the third embodiment of FIG. 18 are represented with like numerals, and their explanations are omitted.

According to the fifth embodiment, the flexible section 44 comprises articular rings 51 to 51d having wire guides 47 to 47d for passing wires 9. Among the wire guides 47 to 47d, the wire guides 47b of the central articular ring 51b are separated farthest from a rear joint 15b of the articular ring 51b. The closer one articular ring is positioned to a front or rear end of the flexible section 44 away from the central articular ring 51b, the nearer the wire guides of the one articular ring approach a rear joint of the one articular ring.

Namely, distances A5 to D5 shown in FIG. 20 have relationships of "B5>A5" and "B5>C5>D5."

With this arrangement, the central articular ring 51b having the longest distance B5 requires a smallest operating force on the wires 9 in bending the flexible section 44. Namely, the central articular ring 51b pivots at first with a small force.

Figure 21:
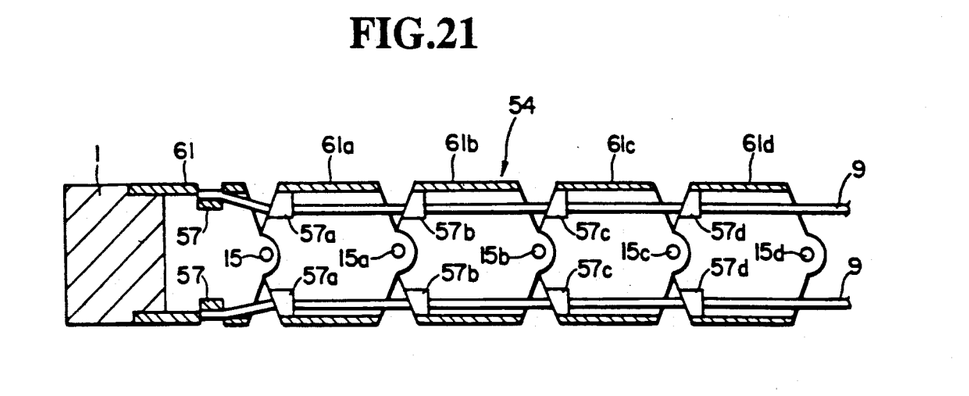
FIG. 21 is a longitudinal section showing a flexible section of an endoscope according to a sixth embodiment of the present invention.

FIG. 21 is a longitudinal section showing a flexible section 54 according to the sixth embodiment of the present invention. In this figure, the same parts as those of the third embodiment of FIG. 18 are represented with like numerals, and their explanations are omitted.

According to the sixth embodiment, the flexible section 54 comprises articular rings 61 to 61d having wire guides 57 to 57d for passing wires 9. The wire guides 57a to 57d are positioned at distal ends away from rear joints 15a to 15d in the respective articular rings 61a to 61d.

When one of the wires 9 is pulled, forces acting on the wire guides 57 to 57d of the articular rings 61a to 61d are most effectively converted into curving forces, so that a wire operating force for orienting the flexible section 54 toward a target may be minimized. In the fifth and sixth embodiments, the positions of the wire guides of at least one articular ring are axially different from the positions of the wire guides of the other articular rings in the axially direction of the rings.

Figure 22:
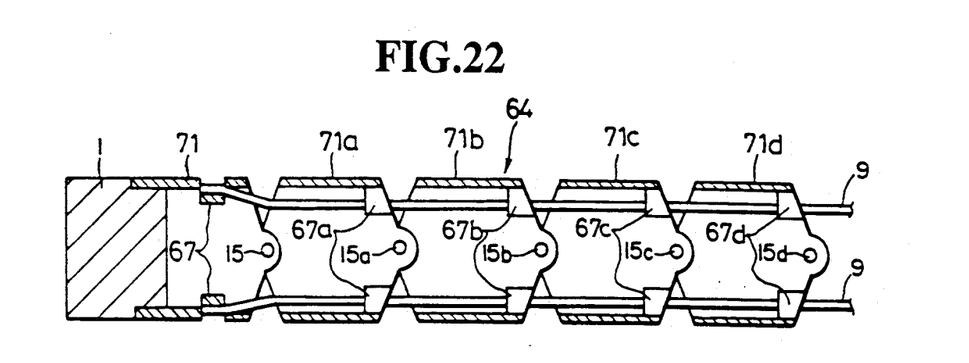
FIGS. 22 and 23 are longitudinal sections showing flexible sections of comparison examples for the sixth embodiment of FIG. 21.
Figure 23:
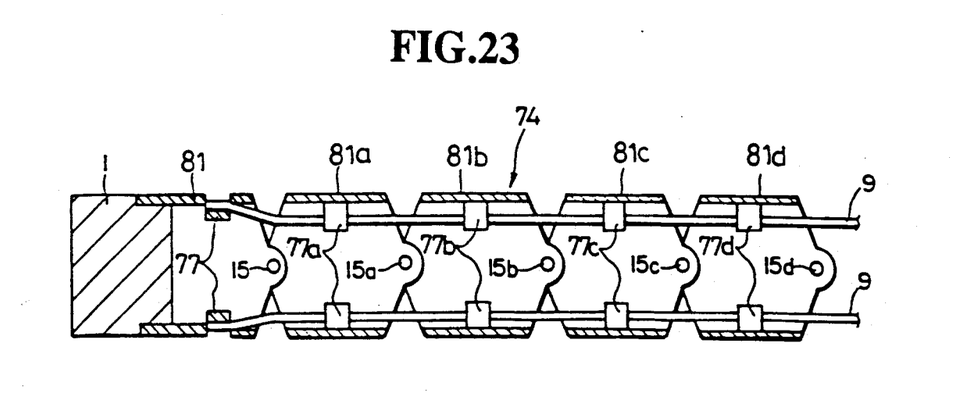

The sixth embodiment of FIG. 21 will be compared with comparison examples of FIGS. 22 and 23.

In a flexible section 64 of FIG. 22, wire guides 67a to 67d for passing wires 9 are positioned proximal to rear joints 15a to 15d in articular rings 71a to 71d, respectively. When one of the wires 9 is pulled, forces acting on the wire guides 67a to 67d of the respective articular rings are inefficiently converted into bending forces, so that a very large wire operating force may be needed to orient the flexible section 64 toward a target.

In FIG. 23, a flexible section 74 has articular rings 81a to 81d. In any one of the articular rings, wire guides (77a, 77b, ..., 77d) for passing wires 9 are positioned at the center of the articular ring.

Figure 24:
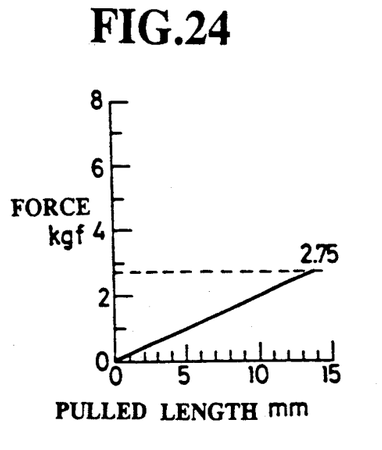
FIGS. 24 to 26 are graphs of test results showing relationships between pulled lengths and operating forces of wires of the flexible sections of FIGS. 21 to 23, respectively.
Figure 25:
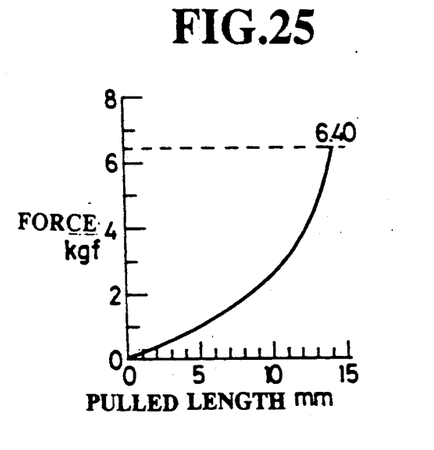
Figure 26:
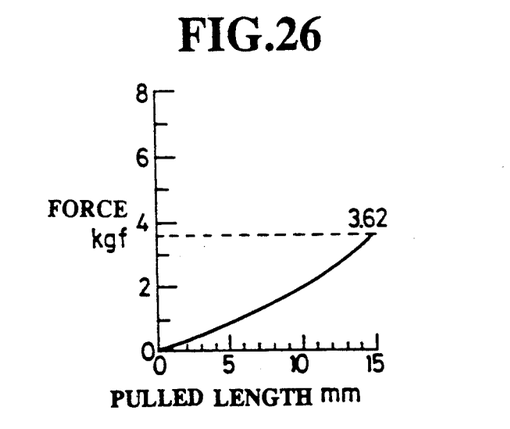

FIG. 24 is a graph of test results showing pulled lengths and operation forces of the flexible section 54 of the sixth embodiment of FIG. 21; FIG. 25 is a graph showing similar test results but of the flexible section 64 of FIG. 22; and FIG. 26 is a graph showing similar test results but of the flexible section 74 of FIG. 23. A final wire operating force of the flexible section 54 of the sixth embodiment of FIG. 21 is 2.75 Kg, which is considerably smaller than 6.40 Kg of the flexible section 64 of FIG. 22, and 3.62 Kg of the flexible section 74 of FIG. 23. This is because the flexible section 54 of the sixth embodiment can effectively convert a wire operating force into a bending moment.

In any one of the first to sixth embodiments, the wire guides are straightly arranged without longitudinally twisting so that the wires can smoothly move in the wire guides compared with conventional arrangements.

As a result, the flexible section of the present invention can be bent with a small wire operating force, and the wires and fibers disposed inside the flexible section of the present invention may not be damaged. Since the wire guides are disposed on the inner wall of the articular rings according to the present invention, a filling ratio of the flexible section for accommodating fibers and tubes may not deteriorate.

Figure 27:
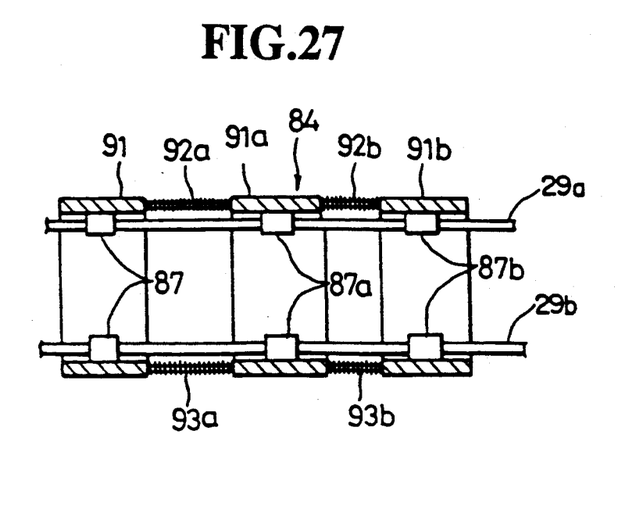
FIG. 27 is a modification of the flexible section according to the present invention.

In the above embodiments, the adjacent articular rings are connected to each other with pivotal shafts to form rotary joints. This arrangement does not limit the present invention. FIG. 27 shows one modification of the invention. In the figure, a flexible section 84 has articular rings 91 to 91b in which adjacent articular rings 91 and 91a, and 91a and 91b are connected to each other with pairs of tension coils 92a and 93a, and 92b and 93b, respectively. These pairs of tension coils form joints. The articular rings 91 to 91b have wire guides 87 to 87b for passing wires 29a and 29b.

When the wire 29a is pulled in the flexible section 84, the tension coils 92a and 92b buckle so that the flexible section 84 may curve on the side of the tension coils 92a and 92b. The lengths, elastic module, etc., of the tension coils 92a to 93b may properly be set so that the flexible section 84 may provide the same functions as those provided by the other embodiments.

The flexible section of any one of the embodiments is applicable not only for endoscopes but also for other devices such as manipulators.

In summary, the present invention changes longitudinal lengths of articular rings of a flexible section of an endoscope, or shifts longitudinal positions of wire guides in a flexible section, thereby providing various flexible sections of endoscopes that are operated with different operation forces and curved in different shapes.

Various modifications will become possible for those skilled in the art after receiving the teachings of the present disclosure without departing from the scope thereof.

What is claimed is:

1. An endoscope having a flexible section, comprising:
    (a) a plurality of articular rings connected to one another to form the flexible section, said articular rings being movable relative to one another, the axial length of at least one of said articular rings being different from the axial length of the other articular rings;
    (b) wire guides disposed in said articular rings; and
    (c) wires passing through said wire guides of said articular rings, for bending the flexible section.

2. The endoscope according to claim 1, wherein one of optional two of said articular rings that is closer to a first end of the flexible section has a longer axial length than the other that is closer to a second end of the flexible section.

3. The endoscope according to claim 1, wherein one of optional two of said articular rings that is closer to a second end of the flexible section has a longer axial length than the other that is closer to a first end of the flexible section.

4. The endoscope according to claim 1, wherein said articular rings are connected to one another through joints so that said articular rings may move relative to one another.

5. The endoscope according to claim 4, wherein an inter-joint distance between front and rear joints of one of said articular rings that is closest to a second end of the flexible section is the shortest among inter-joint distances of the articular rings.

6. The endoscope according to claim 5, wherein the closer one articular ring is positioned to a first end of the flexible section, the longer the inter-joint distance of the one articular ring becomes.

7. The endoscope according to claim 5, wherein the second end of the flexible section is connected to a front end tip having an observation and operation means and the first end of the flexible section is connected to one end of a flexible tube whose another end is connected to a controller having an operation mechanism.

8. The endoscope according to claim 4, wherein an inter-joint distance between front and rear joints of one of said articular rings that is closest to a second end of the flexible section is the longest among inter-joint distances of the articular rings.

9. The endoscope according to claim 8, wherein the closer one articular ring is positioned to a first end of the flexible section, the shorter the inter-joint distance of the one articular ring becomes.

10. The endoscope according to claim 8, wherein the second end of the flexible section is connected to a front end tip having an observation and operation means, and the first end of the flexible section is connected to one end of a flexible tube whose another end is connected to a controller having an operation mechanism.

11. An endoscope having a flexible section, comprising:
    (a) a plurality of articular rings connected to one another to form the flexible section, said articular rings being movable relative to one another;
    (b) wire guides disposed in said articular rings, positions of said wire guides in at least one of said articular rings being axially different from positions of the wire guides of the other articular rings in an axially direction of the rings; and
    (c) a wire passing through said wire guides of said articular rings, for bending the flexible section.

12. The endoscope according to claim 11, wherein one of optional two of said articular rings that is closer to a first end of the flexible section has a longer wire guide distance than the other that is closer to a second end of the flexible section, the wire guide distance being, in any one of the articular rings, a distance measured from an end of the articular ring in question on the first end side of the flexible section to the wire guide of the articular ring in question.

13. The endoscope according to claim 11, wherein one of optional two of said articular rings that is closer to a second end of the flexible section has a longer wire guide distance than the other that is closer to a first end of the flexible section, the wire guide distance being, in any one of the articular rings, a distance measured from an end of the articular ring in question on the second end side of the flexible section to the wire guide of the articular ring in question.

14. The endoscope according to claim 11, wherein each of said articular rings has at least two wire guides, and the wire guides of the at least one of said articular rings are differently positioned from each other.

15. The endoscope according to claim 11, wherein the wire guides are positioned at axial ends of the respective articular rings.

16. A bending tube having a flexible section, comprising;

(a) a plurality of articular rings connected to one another to form relative to one another, the axial length of at least one of said articular rings being different from the axial length of the other articular rings;

(b) wire guides disposed in said articular rings; and (c) wires passing through said wire guides of said articular rings, for bending the flexible section.

17. The bending tube according to claim 16, wherein one of optional two of said articular rings that is closer to a first end of the flexible section has a longer axial length than the other that is close to a second end of the flexible section.

18. The bending tube according to claim 16, wherein one of optional two of said articular rings that is closer to a second end of the flexible section has a longer axial length than the other that is closer to a first end of the flexible section.

19. The bending tube according to claim 16, wherein said articular rings are connected to one another through joints so that said articular rings may move relative to one another.

20. The bending tube according to claim 19, wherein an inter-joint distance between front and rear joints of one of said articular rings that is closest to a second end of the flexible section is the shortest among inter-joint distances of the articular rings.

21. The bending tube according to claim 20, wherein the closer one articular ring is positioned to a first end of the flexible section, the longer the inter-joint distance of the one articular ring becomes.

22. The bending tube according to claim 19, wherein an inter-joint distance between front and rear joints of one of said articular rings that is closest to a second end of the flexible section is the longest among inter-joint distances of the articular rings.

23. The bending tube according to claim 22, wherein the closer one articular ring is positioned to a first end of the flexible section, the shorter the inter-joint distance of the one articular ring becomes.

24. A bending tube having a flexible section, comprising:

(a) a plurality of articular rings connected to one another to form the flexible section, said articular rings being movable relative to one another;

(b) wire guides disposed in said articular rings, positions of said wire guides in at least one of said articular rings being axially different from positions of the wire guides of the other articular rings in an axially direction of the rings; and (c) a wire passing through said wire guides of said articular rings, for bending the flexible section.

25. The bending tube according to claim 24, wherein one of optional two of said articular rings that is closer to a first end of the flexible section has a longer wire guide distance than the other that is closer to a second end of the flexible section, the wire guide distance being, in any one of the articular rings, a distance measured from an end of the articular ring in question on the first end side of the flexible section to the wire guide of the articular ring in question.

26. The bending tube according to claim 24, wherein one of optional two of said articular rings that is closer to a second end of the flexible section has a longer wire guide distance than the other that is closer to a first end of the flexible section, the wire guide distance being, in any one of the articular rings, a distance measured from an end of the articular ring in question on the second end side of the flexible section to the wire guide of the articular ring in question.

27. The bending tube according to claim 24, wherein each of said articular rings has at least two wire guides, and the wire guides of the at least one of said articular rings are differently positioned from each other.

28. The bending tube to claim 24, wherein the wire guides are positioned at axial ends of the respective articular rings.

* * * * *